United States Patent [19]
Suzuki

[11] Patent Number: 6,063,822
[45] Date of Patent: May 16, 2000

[54] METHOD FOR DEWATERING AND PURIFYING OIL OR FAT

[75] Inventor: Masahiro Suzuki, Nara, Japan

[73] Assignee: Novo Nordisk A/S, Bagsvaerd, Denmark

[21] Appl. No.: 09/155,136

[22] PCT Filed: Apr. 18, 1997

[86] PCT No.: PCT/DK97/00173

§ 371 Date: Sep. 16, 1998

§ 102(e) Date: Sep. 16, 1998

[87] PCT Pub. No.: WO97/40123

PCT Pub. Date: Oct. 30, 1997

[30] Foreign Application Priority Data

Apr. 22, 1996 [JP] Japan ..................................... 8-100185

[51] Int. Cl.⁷ ............................... A23D 7/02; C11B 3/00; C11C 1/04; C12N 9/20
[52] U.S. Cl. ........................... 521/55; 521/84.1; 435/198; 435/134; 435/144
[58] Field of Search .................... 521/55, 84.1; 435/198, 435/134, 144

[56] References Cited

U.S. PATENT DOCUMENTS 4,629,742  12/1986  Brady et al. .............................. 521/55
5,677,160  10/1997  Oester et al. ........................... 435/198

FOREIGN PATENT DOCUMENTS 0 622 446 A2  11/1994  European Pat. Off. .

*Primary Examiner*—Nathan M. Nutter
*Attorney, Agent, or Firm*—Steven T. Zelson, Esq.; Reza Green, Esq.

[57] ABSTRACT

The present invention provides methods for reducing the water content of an oil or fat sample, which are carried out by treating the sample with a lipolytic enzyme. Substances that are insoluble in oil or fat, which are precipitated as a result of the water-removing method, may then be removed to purify the oil or fat. The purified oil or fat may also be hydrolyzed to produce hydrolysates of oil or fat.

10 Claims, No Drawings

METHOD FOR DEWATERING AND PURIFYING OIL OR FAT

CROSS-REFERENCE TO RELATED APPLICATIONS

This application is a 35 U.S.C. 371 national application of PCT/DK97/00173 filed Apr. 18, 1997 and claims priority under 35 U.S.C. 119 of Japanese application 8/100185 filed Apr. 22, 1996, the contents of which are fully incorporated herein by reference.

TECHNICAL FIELD OF THE INVENTION

The present invention relates to a method for enzymatically dewatering, drying, isolating and purifying oil or fat. More specifically, it relates to a method for partially hydrolyzing the oil or fat with a lipolytic enzyme, thereby removing water from the oil or fat. It also relates to a method for removing, from oil or fat, substances dispersed therein along with water present in the oil or fat, thereby purifying the oil or fat. Finally, the invention relates to a method for producing a hydrolysate of the purified oil or fat.

BACKGROUND ART

Conventional methods for dewatering and drying substances such as oils and fats include heating the substance, reducing the pressure around the substance, adding a desiccant to the substance, or a combination of these. However, the heating and the pressure reduction require much energy necessary for vaporizing water. In particular, the pressure reduction on an industrial scale further requires vacuum equipment which is expensive. For the addition of desiccant, a large amount of desiccant must be added, resulting in the formation of a water-absorbed desiccant residue that has at least the same volume as that of the water absorbed, which requires the post-treatment of such a large amount of wastes.

Where industrial products are produced from oil or fat (for example, where oil or fat is hydrolyzed to produce diglycerides, monoglycerides, fatty acids or glycerin), the starting oil or fat is often pre-purified in order to reduce the content of the impurities to be in the products. To remove water-soluble substances from raw oil or fat, the raw oil or fat may be washed with water. However, the washing produces a large amount of wastes that must be post-treated.

Heretofore, lipases have been used for hydrolysis, esterification and interesterification of oil or fat. However, there is no precedent for the case of using lipases for dewatering, for drying and even for purifying oil or fat.

One object of the present invention is to provide a simple process for reducing water in oil or fat and for purifying oil or fat. Another object of the present invention is to provide a process useful for obtaining hydrolysates of oil or fat.

MEANS FOR SOLVING THE PROBLEMS

We, the present inventors have assiduously studied in order to attain the above-mentioned objects and, as a result, have surprisingly developed a method for reducing water in oil or fat, which comprises treating a water-containing oil or fat with a lipolytic enzyme to thereby reduce the amount of water in the oil or fat through water-consuming hydrolysis. In addition, we have found that the reduction in the water content of oil or fat can be used for the removal, from the oil or fat, of substances (water-soluble substances, substances insoluble in oil or fat) dispersed in the oil or fat along with the water present therein, without adding any additional water to the oil or fat, thereby achieving purification of the oil or fat. Further, we have found that the oil or fat thus having a reduced content of water and impurities can be effectively used as a starting material for producing hydrolysates of the oil or fat. On the basis of these findings, we have completed the present invention.

Accordingly, the invention provides:
1. A method for reducing water in water-containing oil or fat, which comprises treating the oil or fat with a lipolytic enzyme.
2. A method for removing, from a water-containing oil or fat, a substance which is soluble in water, but insoluble or hardly soluble in the oil or fat, which method comprises:
    a) reducing water from the oil or fat so as to precipitate said substance, and
    b) removing the precipitated substance.
3. A method for producing a hydrolysate of oil or fat, which comprises the following sequential steps:
    a) reducing water in an oil or fat which contains water and a substance that is soluble in water, but insoluble or hardly soluble in the oil or fat so as to precipitate said substance,
    b) removing the precipitated substance,
    c) adding water, and
    d) hydrolyzing the resulting oil or fat.

Now, the present invention is described in detail hereinunder.

Oil or Fat

The oil or fat to be treated according to the present invention may comprise esters of fatty acids, of which the number of carbon atoms is such that lipolytic enzymes can easily act thereon, for example, triglycerides, diglycerides, monoglycerides and wax esters. The number of carbon atoms of the fatty acid moieties, on which lipolytic enzymes can easily act, varies, depending on the type of the lipolytic enzyme, but may be generally from 4 to 28.

The ester content of the oil or fat may be at least equivalent on a molar basis to the amount of water to be removed. Preferably, the ester content is at least 3 times of the equivalent of the water content. The water content to be reduced may be freely determined by those skilled in the art who carry out the method of the present invention.

Lipolytic Enzyme

The lipolytic enzymes for use in the present invention are those that can hydrolyze ester bonds in oil or fat. Such enzymes include, for example, lipases, such as triacylglycerol lipase (EC 3.1.1.3), lipoprotein lipase (EC 3.1.1.34), monoglyceride lipase (EC 3.1.1.23); and esterase (EC 3.1.1.1, EC 3.1.1.2). The numbers in parentheses are the systematic numbers assigned by the Enzyme Commission of the International Union of Biochemistry in accordance with the type of the enzymatic reactivity of the enzyme.

The enzyme can be obtained from microorganisms (such as fungi, yeasts and bacteria), animals (e.g., porcine pancreas), and plants (e.g., wheat malt). Examples of microbial enzymes are lipases derived from the genus Fusarium, Humicola, Thermomyces, Botryosphaeria, Aeromonas, Absidia, Candida, Hyphozyma, Streptomyces, Pseudomonas, Acinetobacter, Alcaligenes, Achromobacter, Rhizomucor, Aspergillus, Penicillium, Chromobacterium or Bacillus, more specifically from the species *Aspergillus niger, Candida cylindracea, Candida lipolytica, Chromobacterium viscosum, Penicillium cyclopium, Pseudomonas solanacearum, Pseudomonas mendocina*

It is preferred to use an enzyme that has a sufficient activity under the conditions used in the process (such as the temperature and pH of the reaction system, the length of the carbon chains of the fatty acid moieties constituting oil or fat, the type of the esters, such as monoglycerides, diglycerides, triglycerides and wax esters, constituting oil or fat). For example, where water is removed from triolein having a water content of about 1% at room temperature according to the present invention, an enzyme that is active under neutral to weakly acidic conditions at room temperature may be used (for example, lipase derived from *Candida cylindracea*, see N. Tomizuka, Y. Ota and K. Yamada, Agr. Biol. Chem., 30, 576, 1966). For oil or fat comprising monoglycerides, an enzyme having a high activity on monoglycerides may be used (for example, monoglyceride lipase, see S. Okumura, M. lwai and Y. Tsujisaka, J. Biochem., 87, 205, 1980). For oil or fat comprising fatty acid moieties having short carbon chains (with from 4 to 8 carbons), an enzyme having a high activity on short-chain fatty acid esters may be used (for example, lipase derived from *Penicillium cyclopium*, see M. Iwai, Y. Tsujisaka, S. Okumura and H. Katsumoto, Oil Chemistry, 29, 587,1980).

For high-temperature treatment of oil or fat, an enzyme having a high activity at high temperatures may be used (for example, lipase derived from *Pseudomonas solanacearum* SD709).

The strain SD709 has been deposited at National Institute of Bioscience and Human-Technology, Agency of Industrial Science and Technology, No. 1–3, Higashi 1 chome Tsukuba-shi Ibaraki-ken 305, Japan. The deposit was made on Dec. 28, 1995 under the terms of the Budapest Treaty with the deposit number FERM BP-5358. It was made by Showa Denko K. K., Japan, and was later assigned to Novo Nordisk A/S.

As described in WO 96/27659, *Pseudomonas solanacearum* SD709 produces a lipase having the following properties:
(1) Action:
   It acts on glycerides, and hydrolyzes the esters.
(2) Substrate Specificity:
   It broadly hydrolyzes various glycerides and esters.
(3) pH at which the enzyme is active; pH optimum:
   When measuring the activity of the enzyme on a triolein emulsion as substrate at pH from 4 to 12, the enzyme is active in the entire range from pH 4 to pH 12 and has optimum activity in the pH range from 6.5 to 9.5.
(4) Temperature at which the enzyme is active; temperature optimum:
   When measuring the activity of the enzyme on a triolein emulsion as substrate at temperatures from 30 to 100° C., the enzyme is active in the entire range from 30 to 100° C. and has optimum activity in the range from 85 to 100° C.
   When measuring the activity of the enzyme on a triolein emulsion as substrate in the presence of 5 mM EDTA (ethylenediamine-tetraacetic acid) at temperatures from 30 to 100° C., the enzyme is active in the entire range from 30 to 100° C. and has optimum activity in the range from 80 to 90° C.
(5) Temperature-dependent Stability:
   After treatment at 80° C. and pH 7 for 1 hour, the enzyme still retains 100% activity.
(6) Molecular Weight:
   The molecular weight of the enzyme as measured through SDS-polyacrylamide gel electrophoresis is 32,000±2,000.
(7) Isoelectric Point:
   The isoelectric point of the enzyme as measured through isoelectric point polyacrylamide gel electrophoresis is 8.8±0.5.
Reaction of Oil or fat with Enzyme
   The reaction conditions of temperature and pH may be controlled to such conditions where the enzyme is active on oil or fat. The means of controlling the pH condition is not specifically limited; for example, it may be effected by adding an acid, an alkali or a pH buffer to the water-containing oil and fat.

Thus, when using an enzyme having a high activity at alkaline pH (for example, lipase derived from *Pseudomonas mendocina*, see Japanese Patent Application Laid-Open No. 6-38746), aqueous ammonia having a concentration of about 0.03% (v/v) or so may be added to the oil or fat to adjust the pH to the range within which the lipase is active, prior to the enzymatic treatment. When using a heat-resistant lipase (for example, lipase derived from *Pseudomonas solanacearum* SD709), the enzymatic treatment may be conducted at 80° C. At such a high temperature, the enzyme can be mixed easily with an oil or fat having a high melting point, such as tristearin, and the enzymatic reaction of such oil or fat is also easy.

The form of the enzyme for use in the present invention is not specifically limited; it may be in powder, liquid, fixed or immobilized form.

The amount of the enzyme to be added may be determined, depending on the above-mentioned reaction conditions, the reaction time and the intended residual amount of water in the oil or fat after the treatment. In general, the amount of enzyme may be from 0.01 to 50000 U per gram of oil or fat to be treated. For example, if the reaction time is desired to be shortened, or if the reaction is desired to be conducted at low temperatures, or if a very low residual amount of water in the oil or fat is desired, the amount of the enzyme to be added shall be increased. If, however, the reaction time may be long, or if the reaction may be conducted at high temperatures, or if the desired amount of residual water in the oil or fat may be large, the amount of the enzyme to be added may be reduced.

The reaction time is not specifically limited, but may be generally from 0.1 to 1000 hours, typically from 4 to 48 hours.

Method for Isolation and Purification
   Water present in oil or fat is often emulsified and dispersed therein, and therefore is difficult to remove by simply statically letting the oil or fat stand for a while. In addition, water dispersed in oil or fat often contains water-soluble substances dissolved therein; and oil or fat often adsorbs surface-active substances on the oil-water interfaces. If the amount of water present in such oil or fat is reduced, the aqueous phase and the oil-water interface will disappear, so components that are insoluble or hardly soluble in the oil or fat (for example, salts, proteins, saccharides, some surfactants) will precipitate out. The thus-precipitated components can be removed from the oil or fat by conventional means, for example, by statically letting the oil or fat stand or through centrifugation or filtration. As a result, the components that are insoluble or hardly soluble in oil or fat are removed, and thus the oil or fat is purified. The means of reducing water in the oil or fat in this purification method is not specifically limited, but the above-mentioned enzymatic method of water reduction is preferred.

Method for Producing Hydrolysates of Oil or fat
   The method for producing hydrolysates of oil or fat of the present invention comprises reducing the amount of water in the oil or fat, removing the insoluble substances thus precipitated therein, adding water, and hydrolyzing the resulting purified oil or fat.

The first and second steps are preferably conducted as described above. The last step of hydrolyzing the oil or fat can be conducted by any known method, but preferably by use of a lipolytic enzyme. The recovery of the hydrolysis products after the final hydrolysis can be done by a conventional method. The hydrolysates of oil or fat thus produced include, for example, fatty acids (or salts thereof, e.g. soap), monoglycerides, diglycerides and glycerin.

EXAMPLES

Now, the present invention is described in more detail hereinunder, with reference to the following examples and comparative examples.

The lipolytic activity in the following examples and comparative examples was measured by the method described in JP-A (Japanese Patent Application Laid-Open No.) 2-92281 where the pH value for the enzymatic reaction was 7. The lipases derived from *Candida lipolytica* and *Pseudomonas mendocina* are those described in JP-A 2-92281 and JP-A 6-38746, respectively. The lipase-producing microorganisms employed are *Candida lipolytica* SD-701 (FERM BP-5891) and *Pseudomonas mendocina* SD702 (FERM BP4291), respectively. FERM BP-4291 is freely available from the National Institute of Bioscience and Human-Technology by reference to U.S. Pat. No. 5,454,971.

The strain SD-701 was deposited at National Institute of Bioscience and Human-Technology, Agency of Industrial Science and Technology, No. 1–3, Higashi 1-chome Tsukuba-shi ibaraki-ken 305, Japan under Accession No. FERM P-10137. The deposit was made by Showa Denko K. K., Japan, and was later assigned to Novo Nordisk A/S. The deposit was subsequently transferred to an international deposit under the terms of the Budapest Treaty on Apr. 2, 1997 under the deposit number FERM BP-5891.

The lipase derived from *Pseudomonas solanacearum* was prepared from *Pseudomonas solanacearum* SD709 according to the method mentioned below.

Two liters of a liquid medium comprising 2% soybean meal, 0.1% diammonium hydrogenphosphate, 0.5% dipotassium hydrogenphosphate, 0.1% magnesium sulfate heptahydrate, 0.3% sodium carbonate and 1% Tween 85 was filled into a 5-liter incubator, sterilized with high-pressure steam at 121° C. for 20 minutes, and inoculated with cells of *Pseudomonas solanacearum* SD709, which were thus incubated therein at 30° C. for 24 hours while stirring with aeration at 1,000 rpm. After the incubation, the cells were removed, and a lipase liquid was obtained. The lipolytic activity of this liquid was 20 U/ml.

The resulting lipase liquid was precipitated with ammonium sulfate, and fractions from 20 to 30% were collected. This was de-salted according to a conventional method, and then lyophilized to obtain a raw lipase powder.

The other reagents used were commercially available. The water content, the nitrogen content and the salt content of the oil or fat were determined according to the method of JIS K2601. The homogenizer used herein was OMNI 2000 (produced by Omni International Co.).

Example 1
Comparison with Dewatering Agents

Water was added to 500 g of olive oil to a water content of about 1%, and this was emulsified with the homogenizer for 10 minutes at 25000 rpm. A lipase or dewatering agent was added thereto as indicated in Table 1, and the mixture was kept at room temperature for 24 hours while stirring. Then, the water content of the treated olive oil was measured. The lipase employed herein was a lipase powder derived from *Candida lipolytica*, having an activity of about 300 U/mg.

TABLE 1

| Lipase or Dewatering Agent | Amount Added | Amount of Water Remained |
|---|---|---|
| Not Added | 0 | 0.98% |
| Lipase | 0.01% | 0.12% |
|  | 0.03% | 0.06% |
|  | 0.1% | 0.01% |
| Anhydrous Calcium Chloride | 0.03% | 0.98% |
|  | 3% | 0.05% |
| Silica Gel | 0.03% | 0.99% |
|  | 3% | 0.79% |

It was found that the lipase employed herein was more effective than the other dewatering agents, even when added in a small amount, and the lipase gave little solid residue after the dewatering treatment.

Example 2
Water Remained after Water-removing Treatment

Water was added to 500 g of triolein to have an initial water content as shown in Table 2, and then emulsified with the homogenizer at 25000 rpm for 10 minutes. As in Example 1, lipase derived from *Candida lipolytica* was added to each sample and left at room temperature for 24 hours with stirring. Then, the water content of each sample was measured.

TABLE 2

| Initial Water Content (%) | Water Remained (%) |
|---|---|
| 5.7 (1 equivalent) | 0.94 |
| 2.0 (3 equivalents) | 0.09 |
| 0.6 (10 equivalents) | 0.05 |
| 0.2 (30 equivalents) | 0.04 |

The figures in parentheses indicate the molar ratio of the esters in oil or fat to water added.

From the data obtained in this example, it is seen that on a molar basis the ester content of the oil or fat may be about equivalent to or higher than the amount of water to be reduced in the oil or fat. Preferably, the ester content is at least 3 times larger than the water amount to be reduced on a molar basis.

Example 3
Type of Lipase, Reaction Conditions

Water was added to 500 g of oil or fat to a water content of about 1%, and this was emulsified with the homogenizer for 10 minutes at 25000 rpm. 50000 U of lipase was added thereto, and reacted under the indicated conditions. The oil or fat and the lipase used herein are shown in Table 3. Oils and fats which are solid at room temperature were heated to complete melting before being used.

TABLE 3

| Lipase Source | Oil or fat | Reaction Time | Temperature | Additive | Water Remained |
|---|---|---|---|---|---|
| Pseudomonas solanacearum | Tristearin | 3 | 80 |  | <0.01% |
|  | Beef Tallow | 6 | 70 |  | <0.01% |
|  | Palm Oil | 12 | 50 |  | 0.02% |
|  | Lanolin | 24 | 80 |  | 0.05% |
| Candida lipolytica | Triolein | 24 | 25 |  | 0.05% |
|  | Diolein | 24 | 25 |  | 0.05% |
|  | Monoolein | 24 | 25 |  | 0.18% |

TABLE 3-continued

| Lipase Source | Oil or fat | Reaction Time | Temperature | Additive | Water Remained |
|---|---|---|---|---|---|
| | Squalene + Triolein (1:1) | 24 | 25 | | 0.07% |
| | Triolein | 96 | 5 | | 0.03% |
| Pseudomonas mendocina | Olive Oil | 24 | 25 | | 0.12% |
| | | 24 | 25 | 0.01% Ammonia | 0.01% |
| | | 24 | 25 | 0.1% CaCO$_3$ | 0.02% |
| Aspergillus niger | Olive Oil | 48 | 25 | 0.02% (NH$_4$)HCO3 | 0.04% |
| Porcine Pancreas | Olive Oil | 96 | 25 | 0.05% K$_2$HPO$_4$ | 0.36% |

As has been demonstrated in Examples 1 to 3, the method of the present invention is effective for reducing water in oil or fat in various combinations of lipase, oil or fat, and reaction conditions. Thus, it is seen that in the method of the present invention the type of lipase to be used, the type of oil or fat to be treated and the reaction conditions to be employed are not specifically restricted.

Example 4
Purification of Oil or fat

A substance as indicated in Table 4 was mixed with 10 ml of water, 500 g of triolein was added, and the resulting mixture was emulsified with a homogenizer at 25000 rpm for 10 minutes. 50000 U of lipase derived from *Pseudomonas solanacearum* was added, and the mixture was reacted at 60° C. for 8 hours with stirring. Next, the reaction mixture was centrifuged to remove the insoluble substances therefrom. Thus was obtained a purified oil. Table 4 shows the amount of the additive added, and the amount of the additive that still remained in the purified oil obtained herein. Of the additives used, egg albumin and chitosan were quantified in terms of the nitrogen content thereof, and salt was in terms of the salinity thereof.

TABLE 4

| Additive | Amount Added to Raw Oil | Amount Remaining in Purified Oil |
|---|---|---|
| Egg Albumin | 0.5% | <0.06% |
| Chitosan | 0.5% | <0.1% |
| Salt | 0.6% | 0.02% |
| Egg Albumin | 0.2% | <0.06% |
| Salt | 0.1% | 0.005% |

It is seen from these results that, according to the method of the present invention, the substances contained in water present in oil or fat (for example, proteins, saccharides, salts) can be removed from the oil or fat without adding any additional water thereto, and the oil or fat can thereby be purified.

Example 5
Purification of Waste Oils

50000 U of lipase derived from *Pseudomonas solanacearum* was added to 500 g of a waste oil, which had been previously filtered through Kim Towel (trade name, product of Jujo Kimberly Co.) to remove precipitate therefrom, and this was reacted at 60° C. for 8 hours with stirring. Next, the reaction mixture was centrifuged to remove the insoluble substances therefrom to obtain a purified oil. Table 5 shows the water content and the nitrogen content of the oil before and after the enzyme treatment. The waste oil used herein was provided by a restaurant, and resulted from the cooking of fried foods. Since the waste oil used herein was found to have a large nitrogen content, the nitrogen content thereof was used as an indication of the purity of the oil.

TABLE 5

| | Before Treatment with Enzyme | After Treatment with Enzyme |
|---|---|---|
| Water Content | 1.8% | 0.01% |
| Nitrogen Content | 0.08% | <0.01% |

Example 6
Production of Salts of Fatty Acids, Monoglyceride and Glycerin from Waste Oil 400 ml of water, 40000 U of lipase derived from *Pseudomonas mendocina* and 0.1 g of ammonium carbonate were added to 400 g of the purified oil from Example 5, and the mixture was reacted at 37° C. for 18 hours with vigorous stirring. The reaction mixture was then centrifuged to separate it into an aqueous phase and an oil phase.

The aqueous phase was concentrated in a rotary evaporator, and then dried in vacuum at about 50° C. 36 g of glycerin was obtained.

10 volumes of water were added to the oil phase. Sodium hydroxide was added to this while stirring to adjust to a pH of 10. Then, this was again centrifuged to separate it into an aqueous phase and an oil phase. The oil phase was washed with 2 volumes of sodium hydroxide solution (pH 10) and water in that order. The resulting wash liquid was combined with the previous aqueous phase. The thus-washed oil phase was dried in vacuum at about 50° C. to give 15 g of monoglyceride. (This oil phase was found to contain at least 92% of monoglyceride, by silica gel thin layer chromatography).

The combined aqueous phase was concentrated in a rotary evaporator and then dried in vacuum at about 50° C. to give 399 g of soap.

A control experiment was made by treating the unpurified waste oil that had been used in Example 5 (that is, the crude waste oil not treated with enzyme) in the same manner. This resulted in 37 g of glycerin, 15 g of monoglyceride and 391 g of soap. Glycerin obtained from the unpurified waste oil was cloudy, but that obtained from the purified oil was transparent. The nitrogen contents of glycerin, monoglyceride and soap produced herein are shown in Table 6. Almost all ammonium carbonate added herein was removed by the vacuum drying, and had little influence on the data in Table 6.

TABLE 6

| | Non-treated Waste Oil | Purified Oil |
|---|---|---|
| Glycerin | 0.7% | 0.01% |
| Monoglyceride | <0.01% | <0.01% |
| Soap | 0.01% | <0.01% |

From the data in Examples 5 and 6, it is seen that waste oil can be purified according to the method of the present invention, and that recovered waste oil can thus be recycled and used as an industrial starting material after purification.

ADVANTAGES OF THE INVENTION

The method of the present invention which is characterized in that water present in oil or fat is reduced through hydrolysis with a lipolytic enzyme is an energy-saving one, and the equipment cost for the method can be reduced. This method can be applied to purification of oil or fat, while reducing wastes (including waste water) to be discharged. By applying this method to recovered waste oils, they can be recycled as industrial materials. For example, the method of the invention is effective for purifying raw oil or fat in the process of obtaining hydrolysates of oil or fat (for example, in the process of starting from triglycerides to give diglycerides, monoglycerides, fatty acids and glycerin). One example of waste oils to which the method of the invention is applicable is a waste oil resulting from the cooking of fried foods. In addition, the method of the present invention for producing hydrolysates of oil or fat is extremely excellent in the point of effective recycle of waste oils.

I claim:

1. A method for reducing the amount of water in an oil or fat sample, wherein said sample contains less than about 2% by weight of water, said method comprising contacting said sample with a lipolytic enzyme under conditions that result in at least about 50% reduction in the water content of said sample.

2. A method as defined in claim 1, wherein said sample contains about 1% or less by weight of water.

3. A method as defined in claim 1, wherein said sample comprises at least one fatty acid ester selected from the group consisting of triglycerides, diglycerides, monoglycerides and wax esters.

4. A method as defined in claim 1, further comprising, prior to said contacting step, adjusting the pH to a value at which said lipolytic enzyme is active.

5. A method as defined in claim 1, wherein said lipolytic enzyme is derived from a microorganism.

6. A method as defined in claim 1, wherein said lipolytic enzyme is a lipase.

7. A method as defined in claim 1, wherein the ester bonds in said sample are present in a molar ratio of at least 3 relative to the molar equivalent of the amount of water in said sample.

8. A method for purifying an oil or fat sample, wherein said sample contains about 2% or less by weight of water, said method comprising:

a) contacting said sample with a lipolytic enzyme under conditions that result in at least about 50% reduction in the water content of said sample, wherein said reduction in water content causes precipitation of at least one substance contained in said sample that is substantially insoluble in said oil or fat; and b) removing said precipitated substance to produce a purified sample.

9. A method for producing a hydrolysate of an oil or fat sample, wherein said sample contains less than about 2% by weight of water, said method comprising:

a) contacting said sample with a lipolytic enzyme under conditions that result in at least about 50% reduction in the water content of said sample, wherein said reduction in water content causes precipitation of at least one substance contained in said sample that is substantially insoluble in said oil or fat;

b) removing said precipitated substance to produce a purified sample, c) adding water to the purified sample of step (b), and d) hydrolyzing the oil or fat.

10. A method as defined in claim 9, wherein said hydrolyzing of step (d) is achieved using a lipolytic enzyme.

* * * * *